United States Patent [19]
Zahiri et al.

[11] Patent Number: 5,693,055
[45] Date of Patent: Dec. 2, 1997

[54] ODD ANGLE INTERNAL BONE FIXATION DEVICE

[76] Inventors: Christopher A. Zahiri; Hormoz Zahiri, both of 11718 Chenault St., Los Angeles, Calif. 90049

[21] Appl. No.: 676,797

[22] Filed: Jul. 8, 1996

Related U.S. Application Data

[63] Continuation-in-part of Ser. No. 367,740, Jan. 3, 1995, abandoned.

[51] Int. Cl.⁶ .................................................. A61B 17/68
[52] U.S. Cl. ............................ 606/69; 606/73; 606/65
[58] Field of Search .............................. 606/65, 66, 67, 606/68, 73, 72, 60, 69, 70, 71

[56] References Cited

U.S. PATENT DOCUMENTS

| | | |
|---|---|---|
| 2,489,870 | 11/1949 | Dzus . |
| 2,526,959 | 10/1950 | Lorenzo . |
| 2,699,774 | 1/1955 | Livingston . |
| 3,489,143 | 1/1970 | Halloran . |
| 4,438,762 | 3/1984 | Kyle . |
| 4,657,001 | 4/1987 | Fixel . |
| 4,973,333 | 11/1990 | Treharne . |

FOREIGN PATENT DOCUMENTS

| | | |
|---|---|---|
| 200251 | 10/1958 | Austria . |
| 828498 | 12/1969 | Canada . |
| 1136123 | 12/1956 | France . |
| 1046827 | 12/1958 | Germany ............................ 606/65 |
| 388740 | 10/1973 | U.S.S.R. . |
| 1250279 | 1/1985 | U.S.S.R. . |
| 868185 | 12/1959 | United Kingdom . |

OTHER PUBLICATIONS

Advertisement for Fracture Appliances, Zimmer, Feb. 1947, 1 page.

*Primary Examiner*—Guy V. Tucker
*Attorney, Agent, or Firm*—Thomas I. Rozsa; Tony D. Chen

[57] ABSTRACT

An odd angle internal fixation device for a transverse fracture located at the junction of the metaphysis and diaphysis of a long bone such as the proximal humerus. The internal fixation device includes an elongated lag screw and a rectangular shaped guide plate. The lag screw is introduced through the diaphyseal segment of the fracture at an angle ranging approximately between 155° to 170°, cross fixing the bone fracture line and settling in the depth of the epiphysis. The guide plate serves as a guide for the lag screw and allows the engagement of the head of the screw to the inner wall of its short barrel. The engagement would cause the rectangular guide plate which is attached to the barrel, to be compressed against the diaphyseal cortex as the screw advances deeper into the epiphysis.

13 Claims, 2 Drawing Sheets

ODD ANGLE INTERNAL BONE FIXATION DEVICE

This application is a Continuation-In-Part of patent application Ser. No. 08/367,740 filed on Jan. 3, 1995, now abandoned.

BACKGROUND OF THE INVENTION

1. Field of the Invention

The present invention relates to the field of medical devices. More particularly, the present invention relates to the field of fixation devices for compressing bone fractures of a human being.

2. Description of the Prior Art

Screw-type compression devices for compressing bone fractures have been used for many years and are well known in the art. At the present time, there is no desirable internal fixation device available for a transverse fracture located at the junction of the metaphysis and diaphysis of a long bone such as the proximal humerus. Currently used devices are either intramedullary nails or a plate and screws.

Unfortunately, the use of intramedullary nails in such fractures is undesirable because of the need for entry at the proximity of the joint, in addition to a need for relatively extensive deep tissue dissection. Moreover, this type of fixation device does not sufficiently stabilize the short proximal segment of a fracture.

Similarly, a plate and screws are also undesirable because of the extent of the surgical approach in the proximity of the joint. In addition, the plate may not be a strong substitute for temporary continuity of the bone to allow freedom of daily activities.

Also, use of screws alone does not provide sufficient temporary mechanical fixation at the fracture site to allow the normal use of the upper or lower extremity for normal daily activities while the fracture is healing.

The following thirteen (13) prior art patents and one (1) advertisement were uncovered in the pertinent field of the present invention:

1. U.S. Pat. No. 2,489,870 issued to Dzus on Nov. 29, 1949 for "Bone Fastening Device" (hereafter "the Dzus Patent");
2. U.S. Pat. No. 2,526,959 issued to Lorenzo on Oct. 24, 1950 for "Fracture Reduction Apparatus" (hereafter "the Lorenzo Patent");
3. U.S. Pat. No. 2,699,774 issued to Livingston on Jan. 18, 1955 for "Bone Pin Locking Device" (hereafter "the Livingston Patent");
4. U.S. Pat. No. 3,489,143 issued to Halloran on Jan. 13, 1970 for "Convertible Hip Pin" (hereafter "the Halloran Patent");
5. U.S. Pat. No. 4,438,762 issued to Kyle on Mar. 27, 1984 for "Orthopedic Hip Fixation Device" (hereafter "the Kyle Patent");
6. U.S. Pat. No. 4,657,001 issued to Fixel on Apr. 14, 1987 for "Antirotational Hip Screw" (hereafter "the Fixel Patent");
7. U.S. Pat. No. 4,973,333 issued to Treharne on Nov. 27, 1990 for "Resorbable Compressing Screw And Method" (hereafter "the Treharne Patent");
8. French Patent No. 1,136,123 (hereafter "the '123 French Patent");
9. Soviet Patent No. 388,740 (hereafter "the '740 Soviet Patent");
10. Soviet Patent No. 1,250,279 (hereafter "the '279 Soviet Patent");
11. Austrian Patent No. 200,251 (hereafter "the '251 Austrian Patent");
12. Canadian Patent No. 828,498 issued to Callender, Jr. on Dec. 2, 1969 for "Fractured Bone Setting Fastener Assembly" (hereafter "the '498 Canadian Patent");
13. British Patent No. 868,185 (hereafter "the '185 British Patent"); and
14. Advertisement For "Fracture Appliances" (hereafter "the Ad").

The Dzus Patent discloses a bone fastening device. It includes a plate and a barrel. It is engaged in a specifically designed screw that requires an extra surgical incision at the contra-lateral side of the bone for its entrance to the bone. It can only be used at a 90° angle. It cannot be used for fixation of a transverse fracture, and transverse osteotomy of the long bones at the proximity of the joints. It is impossible to use it for a joint fusion and for the shoulder area due to the fact that contra-lateral incision for the screw is anatomically almost impossible. The device has a limited use for fixation of a splitting vertical fracture on the large condyles such as distal femoral condyles or proximal tibial condyles.

The Lorenzo Patent discloses a fracture reduction apparatus. It includes a sub-trochanteric bone plate which is fixed to the bone by multiple screws before it can provide a mechanical base for the use of its compression screw.

The Livingston Patent discloses a bone pin locking device. It includes a shell member, a rod and a plate which is fixed to the bone by multiple screws before it can provide a mechanical base for the use of its compression screw.

The Halloran Patent discloses a convertible hip pin. It includes a shank plate which is fixed to the bone by multiple screws before it can provide a mechanical base for the use of its compression screw.

The Kyle Patent discloses an orthopedic hip fixation device. It includes a lag screw, a guide sleeve and a trochanteric plate. The lag screw is telescopically received for slidable movement along the axis of the lag screw within the guide sleeve. A keeper is provided on the lag screw, to capture the lag screw in its telescopic slidable relation in the guide sleeve. The guide sleeve has an extending flange adapted to be received in a slot in the trochanteric plate. The juncture of the flange with the head forms a shoulder which coacts with the plate to assist in fixing a predetermined angle between the plate and the lag screw. The plate is fixed to the bone by multiple screws before it can provide a mechanical base for the use of its compression screw.

The Fixel Patent discloses an antirotational hip screw. It includes a lag screw, a barrel plate and an antirotational/locking pin assembly. There are holes provided on the plate for the use of screws to fix the plate to the bone.

The Treharne Patent discloses a resorbable compressing screw and a method. It includes a hip screw plate which is fixed to the bone by multiple screws before it can provide a mechanical base for the use of its compression screw.

The '123 French Patent, as disclosed from the figures shows a fixation device. It includes a lag screw and an elongated plate which is fixed to the bone by multiple screws before it can provide a mechanical base for the use of its compression screw.

The '740 Soviet Patent discloses a femur neck fraction osteosynthesis bracket. It includes a bracket which is formed of a double angle at the bend transition. The bracket is fixed to the bone by multiple screws before it can provide a mechanical base for the use of its compression screw.

The '279 Soviet Patent discloses a coxofemoral joint arthrodesis device. The device has a plate which is fixed to the bone by multiple screws before it can provide a mechanical base for the use of its compression screw.

The '251 Austrian Patent, as disclosed from the figures shows a fixation device. It includes a lag screw and an elongated plate which is fixed to the bone by multiple screws before it can provide a mechanical base for the use of its compression screw.

The '498 Canadian Patent discloses a fractured bone setting fastener assembly. The device has a plate which is fixed to the bone by multiple screws before it can provide a mechanical base for the use of its compression screw.

The '185 British Patent discloses an improved appliance for use in arthrodesis of the hip joint. It includes a three-flanged nail which is adjacent to flanges to provide a collar for the application of a clamping plate. This is a single purpose device for the hip joint fusion. It has a very high profile system palpable under the skin at the hip area. The plate is anchored and is specifically shaped to the contour of the lateral surface of the femur. The insertion of the device requires an extensive surgical exposure of the inner part of the pelvis through a lower abdominal incision to gain access to the outer part of the acetabulum in order to insert the clamping part of the device over the protruding three-flanged nail.

The Ad discloses screws and a jewett intertrochanteric appliance.

There has been no prior art plate and screw fixation device designed to cross fix a fracture line, osteotomy site or joint fusion at angles between 155° to 170°. Because of the prior art plate design, it requires a large surgical incision and tissue dissection. It is by no means a low profile device and is limited to the proximal femoral area only.

In addition, there has been no prior art plate and screw fixation device that is designed to eliminate the need for the use of extra fixation screws specifically used to maintain the plate against the bone cortex.

It is highly desirable to have a very efficient and also very effective design and construction of an odd angle internal fixation device which is not only functional in providing the necessary stability and guidance in the reduction of the bone fracture, but can be accurately and quickly implanted by the surgeon through a small skin incision and minimal tissue dissection. It is desirable to provide an odd angle internal fixation device for a transverse fracture located at the junction of the metaphysis and diaphysis of a long bone such as the proximal humerus, thereby eliminating the need for deep dissection of the soft tissue in the proximity of the joint. It is also desirable to eliminate the need for the use of extra fixation screws specifically used to maintain the plate against the bone cortex.

SUMMARY OF THE INVENTION

The present invention is a unique odd angle internal fixation device for a transverse fracture located at the junction of the metaphysis and diaphysis of a long bone such as the proximal humerus.

The odd angle internal fixation device includes an elongated lag screw and a rectangular shaped guide plate. The lag screw is introduced through the diaphyseal segment of the fracture at an angle ranging approximately between 155° to 170°, cross fixing the bone fracture line and settling in the depth of the epiphysis. The guide plate serves as a guide for the lag screw and allows the engagement of the head of the lag screw to the inner wall of its short barrel portion. The engagement would cause the guide plate which is attached to the barrel, to be compressed against the diaphyseal cortex as the lag screw advances deeper into the epiphysis at an angle ranging approximately between 155° to 170°.

It has been discovered, according to the present invention, that if an odd angle internal fixation device is provided with a lag screw and a guide plate which has an inclined short barrel portion integrally attached to the guide plate at an angle ranging approximately between 155° to 170°, then it will cross fix a fracture line of the junction of the metaphysis and diaphysis, or cross fix the osteotomy site of the junction of the metaphysis and diaphysis or it can be used for joint fusion.

It has additionally been discovered, according to the present invention, that if the short barrel portion of the guide plate is designed with two different internal diameters, then the lag screw engages the inside of the short barrel portion at two different diameters. This would create the desired precision for the engagement and provides the necessary mechanical advantage for utmost solid compression in the odd angle fixation device.

It has further been discovered, according to the present invention, that if the guide plate is designed to dissipate all the compression forces of the odd angle internal fixation device that are applied against the bone cortex, and practically reduces the forces to an easily tolerable level by the bone cortex, then the repetitive normal use of the upper extremity after fixation cannot cause any failure by loosening of the device because the forces applied are well dissipated around the guide plate, and thereby the bone cortex remains healthy and intact which results in a mechanical advantage not provided by any screw design in the prior art.

It is therefore an object of the present invention to provide an odd angle internal fixation device which can cross fix a fracture line, osteotomy site or joint fusion at an angle ranging approximately between 155° to 170°.

It is an additional object of the present invention to provide a short barrel portion integrally attached to a guide plate and having two different internal diameters, so that a lag screw engages the inside of the short barrel portion at two different diameters and creates the desired precision for the engagement and provides the necessary mechanical advantage for utmost solid compression in the odd angle fixation device.

It is a further object of the present invention to provide a guide plate which can dissipate all the compression forces of the odd angle internal fixation device that are applied against the bone cortex, and practically reduce the forces to an easily tolerable level by the bone cortex. The repetitive normal use of the upper extremity after fixation cannot cause any failure by loosening of the device because the forces applied are well dissipated around the guide plate, and thereby the bone cortex remains healthy and intact.

It is an additional object of the present invention to provide a guide plate which does not need additional fixation screws specifically used to maintain the guide plate against the bone cortex. The odd angle fixation device eliminates any such need, because the fixation of the guide plate against the bone cortex is provided by the main lag screw itself.

It is a further object of the present invention to provide an elongated lag screw which can be different types and shapes but still serves the purpose of engagement into the bone.

It is an additional object of the present invention to provide a guide plate having a short barrel portion which can be produced with angles ranging approximately between 90° to 170° and be used for varieties of fractures, fusion procedures and osteotomies.

The guide plate is designed to serve as a very low profile fixation device palpable over the patient's extremity at the surgical site. The guide plate is far less prominent than the head of a screw, especially when used at an angle.

In the preferred embodiment of the present invention, the odd angle internal fixation device includes an elongated lag screw and a rectangular shaped guide plate which has a short barrel portion at an inclined angle of approximately 155°.

In another embodiment of the present invention, the odd angle internal fixation device includes an elongated lag screw and a rectangular shaped guide plate which has a short barrel portion at an inclined angle of approximately 170°.

In the preferred embodiment of the present invention, a major point of uniqueness is having the odd angle internal fixation device which includes an elongated lag screw and a rectangular shaped guide plate which has a short barrel portion at an inclined angle in the range of from 155° to 170°. However, it should be appreciated that the present invention can also be utilized with a rectangular shaped guide plate which has a short barrel portion at an inclined angle in the range of from 90° to 155° and therefore, the total range of the inclined angle with which the present invention can be utilized, is approximately 90° to approximately 170°.

In still another embodiment of the present invention, the odd angle internal fixation device includes an elongated lag screw and a rectangular shaped guide plate which has a short barrel portion at an inclined angle of approximately 90°.

The present invention is not limited to the three degrees as described above, 90°, 155° and 170°. The short barrel portion of the guide plate can be between 155° to 170°, and it can also be produced with angles ranging between 90° to 155° and be used for varieties of fractures, fusion procedures and osteotomies.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
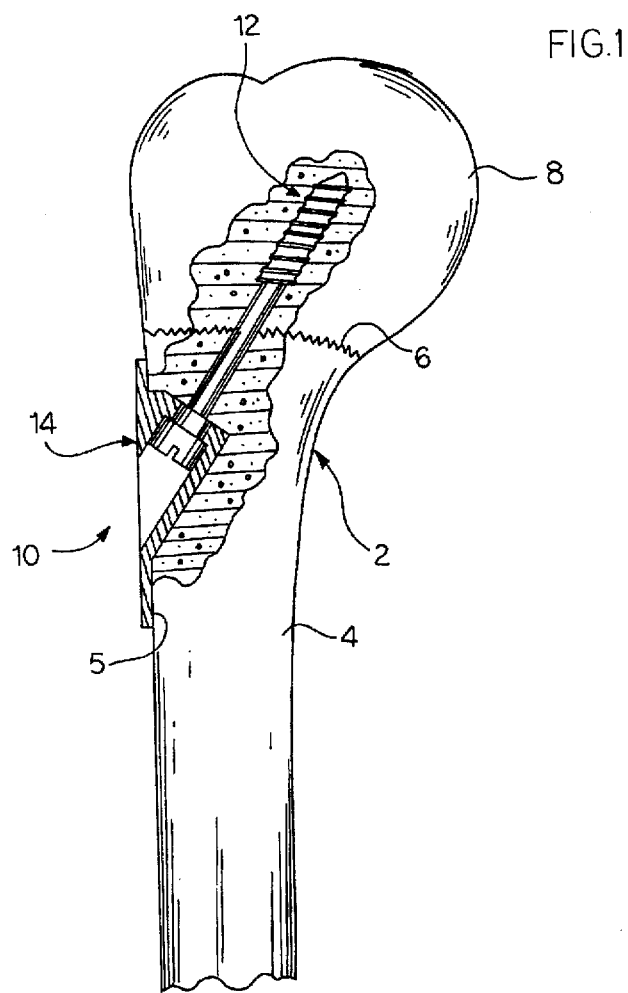
FIG. 1 is a cross-sectional side elevational view of one of the embodiments of the present invention odd angle internal fixation device, showing the device fitted, as it would be used, with portions of the diaphysis being cut away for illustrative purposes.

Referring to FIG. 1, there is shown at 10 one of the embodiments of the present invention odd angle internal fixation device, illustrating the device fitted as it would be used in a fracture of the diaphysis 2. The odd angle internal fixation device 10 is introduced through the diaphyseal segment 4 of the fracture at angles ranging between 155° to 170°, cross fixing the fracture line 6 and settling in the depth of the epiphysis 8.

Figure 2:
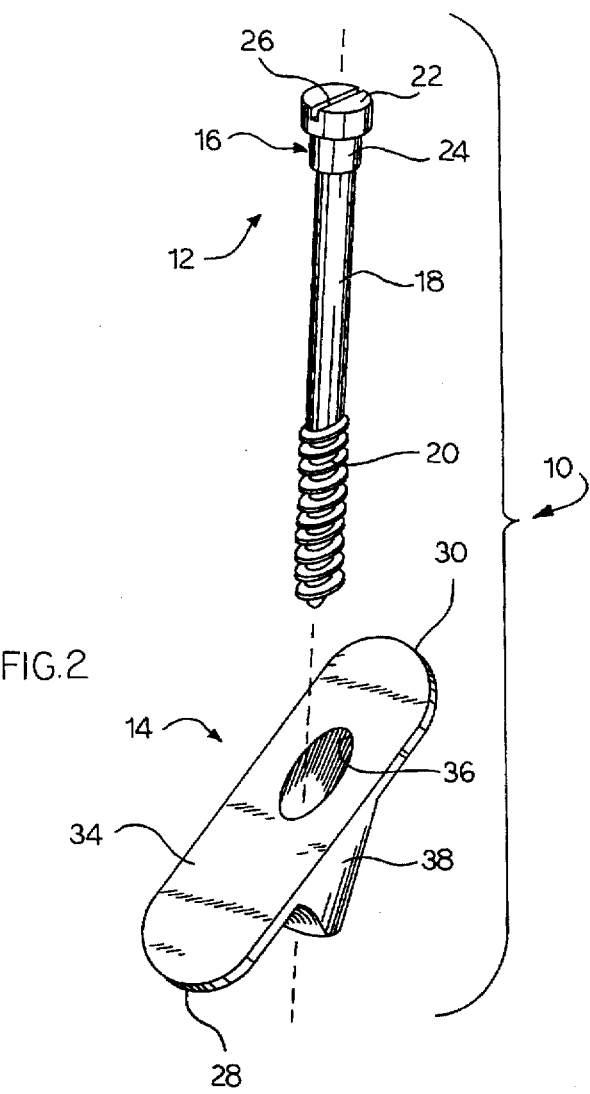
FIG. 2 is an enlarged exploded perspective view the present invention odd angle internal fixation device, shown in the embodiment of FIG. 1.

FIG. 2 shows an enlarged exploded perspective view of the present invention odd angle internal fixation device 10 which includes an elongated lag screw 12 and a generally rectangular shaped guide plate 14. Referring to FIGS. 1 and 2, the lag screw 12 has a proximal portion 16, a middle shaft portion 18 and a distal threaded portion 20. The proximal portion 16 is provided with a proximal head 22 and a proximal shoulder flange 24. The proximal head 22 has a slotted top end 26 which is provided for accommodating a driving tool, such as a flat tip screwdriver to drive the lag screw 12 into the diaphysis 2.

It will be appreciated that the slotted top end 26 is not limited to accommodating the flat tip screwdriver. The proximal head 22 can be manufactured with a cross head top end, so that a cross-headed screwdriver can drive the lag screw 12 into the diaphysis.

One of the unique features of the lag screw 12 is that its has three different diameters. The diameter of the middle shaft portion 18 is less than the diameter of the proximal shoulder flange 24, and the diameter of the proximal shoulder flange 24 is less than the diameter of the proximal head 22. The significance of the different diameters will be described later.

Figure 3:
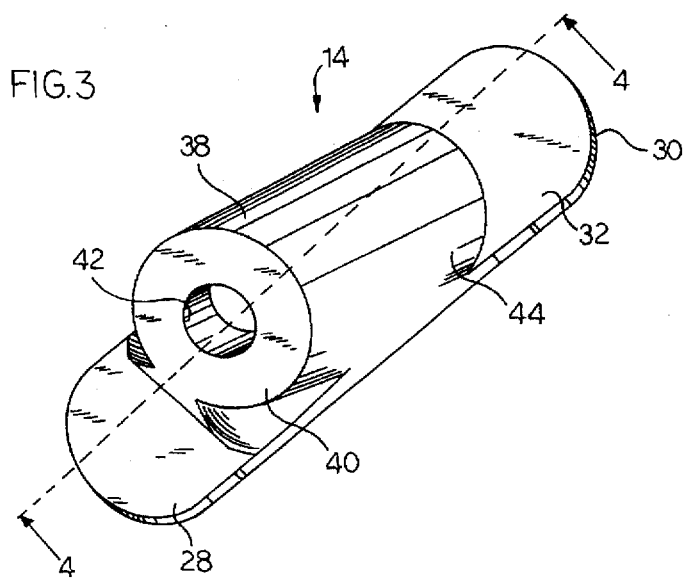
FIG. 3 is an enlarged top perspective view of the rectangular shaped guide plate.
Figure 4:
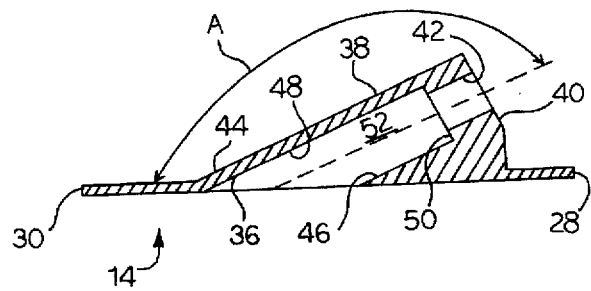
FIG. 4 is a cross-sectional view taken along line 4—4 of FIG. 3, showing the short barrel portion of the guide plate at an angle of 155°.

FIG. 3 shows an enlarged top perspective view of the rectangular shaped guide plate 4. FIG. 4 shows a cross-sectional of the guide plate 4. Referring to FIGS. 2, 3 and 4, the guide plate 14 has two opposite ends 28 and 30, a front side 32, a back side 34, and a bore 36 therethrough which is located off-center and adjacent to one end 30 of the guide plate 14. The two opposite ends 28 and 30 are generally semi-ovular shaped.

Referring to 3 and 4, there is shown a short barrel portion 38 which is integrally attached to the guide plate 14. The short barrel portion 38 has a distal end 40 with an opening 42, a proximal end 44 with an opposite opening 46, an inner sidewall 48, and an inner flange 50. The inner sidewall 48 defines a passage 52 which extends from the distal end opening 42 to the proximal end opening 46, where the internal diameter of the distal end opening 42 is less than the internal diameter of the passage 52. The proximal end 44 of the short barrel portion 38 is integrally attached to the front side 32 of the guide plate 14 at an inclined angle "A" such that the proximal end opening 46 of the barrel portion 38 communicates with the bore 36 of the guide plate 14.

Referring to FIGS. 2 and 4, the operation of the present invention odd angle internal fixation device 10 will be described. The short barrel portion 38 is positioned within a hole formed in the diaphysis 4 by a surgeon, using conventional methods. The lag screw 12 is slidably received within the passage 52 of the barrel portion 38 from the back side 34 of the guide plate 14, where the interior of the short barrel portion 38 is designed so that the lag screw 12 engages into the barrel portion 38 at two different diameters of the passage 52 and the distal end opening 42. When the lag screw 12 is received within the short barrel portion 38, the diameter of the proximal shoulder flange 24 is slightly less than the internal diameter of the distal end opening 42 of the barrel portion 38 and provides a press fitted engagement thereon. The proximal head 22 of the lag screw 14 is slightly less than the internal diameter of the passage 52 of the short barrel portion 38 and provides a press fitted engagement thereon. This would create the desired precision for the engagement and provides the necessary mechanical advantage for utmost solid compression in the odd angle internal fixation device 10.

Once the lag screw 12 is received within the barrel portion 38, the distal threaded portion 20 extends out of the barrel portion 38 and is introduced through the diaphyseal segment 4 of the fracture at angle "A", cross fixing the fracture line 6 and settling in the depth of the epiphysis 8.

The specially designed guide plate 14 serves as a guide for the elongated lag screw 12 and allows the engagement of the proximal head 22 of the lag screw 12 to the inner sidewall 48 of the short barrel portion 38. The engagement would cause the guide plate 14 which is attached to the barrel portion 38, to be compressed against the diaphyseal cortex 5 as the lag screw 12 advances deeper into the epiphysis 8 at angles ranging approximately between 155° to 170°, preferably at an angle of 155°.

Between one to three of the internal fixation devices 10 may provide temporary rigid continuity of the bone such that once the soft tissue healing has taken place, the patient may be allowed to use the arm freely for daily activities with minimal limitations.

The present invention has many advantageous features, e.g., for the proximal humeral fracture, introduction of the internal fixation device 10 into the bone is achieved through a small incision located below the attachment of the deltoid muscle where the humeral diaphysis is easily palpated. As a result, the need for deep dissection of the soft tissue in the proximity of the joint is eliminated. The odd angle internal fixation device 10 can be manufactured in different sizes and used for similar fractures in a variety of joints. The odd angle internal fixation device 10 may be used for solid fixation in osteotomies and in joint fusion. The odd angle internal fixation device 10 can also be manufactured with angles ranging approximately between 90° to 155° and be used for varieties of fractures, fusion procedures and osteotomies. The present invention conforms to conventional forms of manufacture, and is of simple construction and is easy to use.

Figure 5:
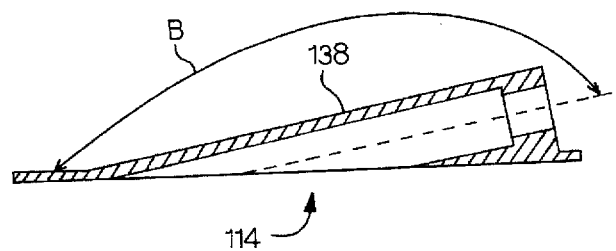
FIG. 5 is a cross-sectional view of another embodiment of the present invention rectangular shaped guide plate, showing the short barrel portion at an angle of 170°.

Referring to FIG. 5, there is shown a cross-sectional view of another embodiment of the present invention odd angle internal fixation device. The parts are numbered correspondingly with 100 added to each number. This embodiment is identical to the first embodiment as previously described in FIGS. 1 through 4 except that the short barrel portion 138 of the guide plate 114 is now at an angle "B" which is approximately 170°. The same elongated lag screw is used with this embodiment, and since it assembles and functions the same as previously described, and the description thereof will not be repeated.

Figure 6:
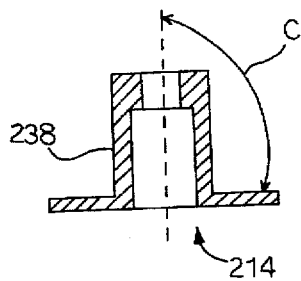
FIG. 6 is a cross-sectional view of still another embodiment of the present invention rectangular shaped guide plate, showing the short barrel portion at an angle of 90°.

Referring to FIG. 6, there is shown a cross-sectional view of still another embodiment of the present invention odd angle internal fixation device. The parts are numbered correspondingly with 200 added to each number. This embodiment is identical to the first embodiment as previously described in FIGS. 1 through 4 except that the short barrel portion 238 of the guide plate 214 is now at an angle "C" which is approximately 90°, perpendicular to the guide plate 214. The same elongated lag screw is used with this embodiment, and since it assembles and functions the same as previously described, the description thereof will not be repeated.

Defined in detail, the present invention is an internal fixation device for use in a transverse surgical neck fracture of the humerus to cross fix a fracture line, the internal fixation device comprising: (a) a generally rectangular shaped low profile guide plate for abutting against the diaphysis cortex of the humerus on one side of the fracture and having a front side, a back side and a bore therethrough located adjacent to one end of the low profile guide plate; (b) a short barrel portion having a distal end with an opening, a proximal end with an opposite opening, an inner sidewall, and an inner flange adjacent to the distal end, the inner sidewall defining a passage extending from the distal end opening to the proximal end opening, the internal diameter of the distal end opening being less than the internal diameter of the passage of the inner sidewall of the barrel portion, the length of the barrel portion being sufficiently short so as not to cross the fracture line and also to rest a sufficient distance from the fracture line to leave a bone mass between the fracture line and the distal end of the short barrel portion; (c) the proximal end of the barrel portion integrally attached to the front side of the low profile guide plate at an inclined angle between 155° to 170° such that the passage is communicating with the bore of the low profile guide plate, the short barrel portion for adapting within the diaphysis cortex of the humerus such that the front side of the low profile guide plate is placed against the diaphysis cortex of the humerus; (d) an elongated lag screw for internally cross fixing the fracture line and settling in the depth of the epiphysis and having a distal threaded portion, a middle shaft portion, and a proximal portion, the proximal portion having a proximal shoulder flange and a proximal head with means for receiving a driving tool in its top end, the diameter of the middle shaft portion being less than the diameter of the proximal shoulder flange, and the diameter of the shoulder flange being less the diameter of the proximal head; and (e) the lag screw being slidably received within the passage of the barrel portion and extending out of the barrel portion for cross fixing the fracture line of the diaphysis cortex of the humerus with the distal threaded portion of the lag screw being located within the depth of the epiphysis, the proximal shoulder flange of the lag screw being press-fitted within the distal end opening of the barrel portion such that the proximal head of the lag screw is contacting the inner flange of the inner sidewall of the short barrel portion and rests within the barrel portion for preventing the proximal head from extending out of the barrel portion when the low profile guide plate is compressed against the diaphysis cortex of the humerus, and the low profile guide plate adapted for being fixed to the diaphysis cortex of the humerus solely by the lag screw and dissipates all of the compression forces of the internal fixation device; (f) whereby the low profile guide plate dissipates all of the compression forces of the internal fixation device that are applied against the diaphysis cortex of the humerus, and thereby the diaphysis cortex of the humerus remains healthy and intact.

Defined broadly, the present invention is a fixation device for use in a transverse surgical neck fracture of the humerus to cross fix a fracture line, the fixation device comprising: (a) a low profile guide plate for abutting against the diaphysis cortex of the humerus on one side of the fracture and having a barrel portion integrally attached to the low profile guide plate at an inclined angle, the barrel portion for adapting within the diaphysis cortex of the humerus and having a distal end with an opening, a proximal end with an opening, an inner sidewall, and an inner flange adjacent to the distal end, the inner sidewall defining a passage extending from the distal end opening to the proximal end opening, where the internal diameter of the distal end opening is less than the internal diameter of the passage of the inner sidewall of the barrel portion, the length of the barrel portion being sufficiently short so as not to cross the fracture line and also rest a sufficient distance from the fracture line and the distal end of the barrel portion; (b) a lag screw for internally cross fixing the fracture line and settling in the depth of the epiphysis and having a distal threaded portion, a middle shaft portion and a proximal portion, the proximal portion having a proximal shoulder flange and a proximal head, the diameter of the middle shaft portion being less than the diameter of the proximal shoulder flange, and the diameter of the proximal shoulder flange being less the diameter of the proximal head; and (c) the lag screw being slidably received within the passage of the barrel portion and extending out of the barrel portion for cross fixing the fracture line of the diaphysis of cortex of the humerus with the distal threaded portion of the lag screw, the proximal shoulder flange of the lag screw being press-fitted within the distal end opening of the barrel portion such that the proximal head of the lag screw is contacting the inner flange of the inner sidewall of the barrel portion for preventing the proximal head from extending out of the barrel portion when the low profile guide plate is compressed against the diaphysis cortex of the humerus, and the low profile guide plate adapted for being fixed to the diaphysis cortex of the humerus solely by the lag screw and dissipates all of the compression forces of the fixation device; (d) whereby the low profile guide plate dissipates all of the compression forces of the fixation device that are applied against the diaphysis cortex of the humerus, and thereby the diaphysis cortex of the humerus remains healthy and intact.

Defined more broadly, the present invention is a fixation device for use in a surgical neck fracture of the humerus to cross fix a fracture line, the fixation device comprising: (a) a low profile guide plate for abutting against the bone codex and having a barrel integrally attached to the low profile guide plate at an inclined angle, the barrel for adapting within the neck fracture of the humerus and having a sidewall, the sidewall defining a passage therethrough and having a flange, the length of the barrel being sufficiently short so as not to cross the fracture line and also to rest a sufficient distance from the fracture line to leave a bone mass between the fracture line and the barrel; and (b) a lag screw having a distal threaded portion and a proximal portion, the lag screw being slidably received within the passage of the barrel and extending out of the barrel for cross fixing the fracture line of the humerus with the distal threaded portion of the lag screw, the flange of the sidewall of the barrel preventing the proximal portion from extending out of the barrel when the low profile guide plate is compressed against the humerus by the lag screw, and the low profile guide plate adapted for being fixed to the bone solely by the lag screw and dissipates all of the compression forces of the fixation device; (c) whereby the low profile guide plate dissipates all of the compression forces of the fixation device that are applied against the humerus, and thereby the humerus remains healthy and intact.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An internal fixation device for use in a transverse surgical neck fracture of the humerus to cross fix a fracture line, the internal fixation device comprising a guide plate and a single screw;

wherein the guide plate comprises
a generally rectangular shaped low profile guide plate for abutting against the diaphysis cortex of the humerus on one side of the fracture and having a front side, a back side and a bore therethrough located adjacent to one end of the low profile guide plate;
a short barrel portion having a distal end with an opening, a proximal end with an opposite opening, an inner sidewall, and an inner flange adjacent to the distal end, the inner sidewall defining a passage extending from the distal end opening to the proximal end opening, the internal diameter of the distal end opening being less than the internal diameter of the passage of the inner sidewall of the barrel portion, the length of the barrel portion being sufficiently short so as not to cross the fracture line and also to rest a sufficient distance from the fracture line to leave a bone mass between the fracture line and the distal end of the short barrel portion;
said proximal end of said barrel portion integrally attached to said front side of said low profile guide plate at an inclined angle between 155° to 170° such that said passage is communicating with said bore of said low profile guide plate, said short barrel portion for adapting within said diaphysis cortex of the humerus such that said front side of said low profile guide plate is placed against the diaphysis cortex of the humerus;

wherein the single screw is
an elongated lag screw for internally cross fixing the fracture line and settling in the depth of the epiphysis and having a distal threaded portion, a middle shaft portion, and a proximal portion, the proximal portion having a proximal shoulder flange and a proximal head with means for receiving a driving tool in its top end, the diameter of the middle shaft portion being less than the diameter of the proximal shoulder flange, and the diameter of the shoulder flange being less the diameter of the proximal head; and
said lag screw being slidably received within said passage of said barrel portion and extending out of said barrel portion for cross fixing the fracture line of said diaphysis cortex of the humerus with said distal threaded portion of said lag screw being located within the depth of the epiphysis, said proximal shoulder flange of said lag screw being press-fitted within said distal end opening of said barrel portion such that said proximal head of said lag screw is contacting said inner flange of said inner sidewall of said short barrel portion and rests within said barrel portion for preventing said proximal head from extending out of said barrel portion when said low profile guide plate is compressed against said diaphysis cortex of the humerus, and said low profile guide plate adapted for being fixed to the diaphysis cortex of the humerus solely by said lag screw and dissipates all of the compression forces of the internal fixation device;

whereby said low profile guide plate dissipates all of the compression forces of said internal fixation device that are applied against said diaphysis codex of the humerus, and thereby said diaphysis codex of the humerus remains healthy and intact.

2. A fixation device for use in a transverse surgical neck fracture of the humerus to cross fix a fracture line, the fixation device comprising a guide plate and a single screw;

wherein the guide plate comprises a low profile guide plate for abutting against the diaphysis codex of the humerus on one side of the fracture and having a barrel portion integrally attached to the low profile guide plate at an inclined angle, the barrel portion for adapting within the diaphysis codex of the humerus and having a distal end with an opening, a proximal end with an opening, an inner sidewall, and an inner flange adjacent to the distal end, the inner sidewall defining a passage extending from the distal end opening to the proximal end opening, where the internal diameter of the distal end opening is less than the internal diameter of the passage of the inner sidewall of the barrel portion, the length of the barrel portion being sufficiently shod so as not to cross the fracture line and also rest a sufficient distance from the fracture line and the distal end of the barrel portion;

wherein the single screw is a lag screw for internally cross fixing the fracture line and settling in the depth of the epiphysis and having a distal threaded portion, a middle shaft portion and a proximal portion, the proximal portion having a proximal shoulder flange and a proximal head, the diameter of the middle shaft portion being less than the diameter of the proximal shoulder flange, and the diameter of the proximal shoulder flange being less the diameter of the proximal head; and said lag screw being slidably received within said passage of said barrel portion and extending out of said barrel portion for cross fixing the fracture line of said diaphysis of cortex of the humerus with said distal threaded portion of said lag screw, saidproximal shoulder flange of said lag screw being press-fitted within said distal end opening of said barrel portion such that said proximal head of said lag screw is contacting said inner flange of said inner sidewall of said barrel portion for preventing said proximal head from extending out of said barrel portion when said low profile guide plate is compressed against said diaphysis cortex of the humerus, and said low profile guide plate adapted for being fixed to the diaphysis cortex of the humerus solely by said lag screw and dissipates all of the compression forces of the fixation device;

whereby said low profile guide plate dissipates all of the compression forces of said fixation device that are applied against said diaphysis cortex of the humerus, and thereby said diaphysis cortex of the humerus remains healthy and intact.

3. The fixation device in accordance with claim 2 wherein said inclined angle of said barrel portion is an obtuse angle in the range of approximately 155° to 170°.

4. The fixation device in accordance with claim 2 wherein said inclined angle of said barrel portion is an obtuse angle in the range of approximately 90° to 155°.

5. The fixation device in accordance with claim 2 wherein said proximal head has a means for accommodating a driving tool.

6. The fixation device in accordance with claim 5 wherein said means for accommodating a driving tool is a slot within the top of said proximal head.

7. A fixation device for use in a surgical neck fracture of the humerus to cross fix a fracture line, the fixation device comprising:

a guide plate and a single screw;

wherein the guide plate comprises a low profile guide plate for abutting against the bone cortex and having a barrel integrally attached to the low profile guide plate at an inclined angle, the barrel for adapting within the neck fracture of the humerus and having a sidewall, the sidewall defining a passage therethrough and having a flange, the length of the barrel being sufficiently short so as not to cross the fracture line and also to rest a sufficient distance from the fracture line to leave a bone mass between the fracture line and the barrel; and wherein the single screw is a lag screw having a distal threaded portion and a proximal portion, the lag screw being slidably received within said passage of said barrel and extending out of said barrel for cross fixing the fracture line of the humerus with the distal threaded portion of the lag screw, said flange of said sidewall of said barrel preventing said proximal portion from extending out of said barrel when said low profile guide plate is compressed against said humerus by the lag screw, and said low profile guide plate adapted for being fixed to the bone solely by the lag screw and dissipates all of the compression forces of the fixation device;

whereby said low profile guide plate dissipates all of the compression forces of said fixation device that are applied against said humerus, and thereby said humerus remains healthy and intact.

8. The fixation device in accordance with claim 7 wherein said inclined angle of said barrel is an obtuse angle in the range of approximately 155° to 170°.

9. The fixation device in accordance with claim 7 wherein said inclined angle of said barrel is an obtuse angle in the range of approximately 90° to 155°.

10. The fixation device in accordance with claim 7 wherein said passage of said barrel has two different internal diameters.

11. The fixation device in accordance with claim 7 wherein said proximal portion of said lag screw includes a proximal shoulder flange and a proximal head, where the diameter of the shoulder flange is less than the diameter of the proximal head.

12. The fixation device in accordance with claim 11 wherein said proximal head of said proximal portion of said lag screw has a means for accommodating a driving tool.

13. The fixation device in accordance with claim 12 wherein said means for accommodating a driving tool is a slot in the top end of said proximal head.

* * * * *